United States Patent [19]

Humphrey et al.

[11] Patent Number: 4,968,703

[45] Date of Patent: Nov. 6, 1990

[54] PHARMACEUTICAL COMPOSITIONS FOR THE TREATMENT OF OCCLUSIVE VASCULAR DISEASES

[75] Inventors: Patrick P. A. Humphrey, Wrestlingworth; Philip Lumley, Ware, both of England

[73] Assignee: Glaxo Group Limited, London, England

[21] Appl. No.: 379,372

[22] Filed: Jul. 13, 1989

Related U.S. Application Data

[63] Continuation-in-part of Ser. No. 82,500, Aug. 7, 1987, abandoned.

[30] Foreign Application Priority Data

Aug. 8, 1986 [GB] United Kingdom ............... 8619450
Aug. 31, 1988 [GB] United Kingdom ............... 8820578

[51] Int. Cl.$^5$ .......................................... A01N 43/40
[52] U.S. Cl. ................................................ 514/315
[58] Field of Search ...................................... 514/315

[56] References Cited

U.S. PATENT DOCUMENTS 4,388,324 6/1983 Harrobin ............................ 514/315
4,568,676 2/1986 Smith ................................. 514/315
4,694,012 9/1987 Archibald et al. ................. 514/315

FOREIGN PATENT DOCUMENTS 2097397 11/1982 United Kingdom .

*Primary Examiner*—Curtis R. Davis
*Attorney, Agent, or Firm*—Bacon & Thomas

[57] ABSTRACT

The use is described of both (i) [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid or a physiologically acceptable salt or solvate thereof and (ii) a thromboxane synthase inhibitor, either separately or in combination in the therapy or prophylaxis of occlusive vascular diseases in humans.

Pharmaceutical compositions containing both (i) and (ii) are also described.

19 Claims, No Drawings

PHARMACEUTICAL COMPOSITIONS FOR THE TREATMENT OF OCCLUSIVE VASCULAR DISEASES

CROSS-REFERENCE TO RELATED APPLICATION

This application is a continuation-in-part of application Ser. No. 082,500, filed Aug. 7, 1987, now abandoned.

This invention relates to improvements in the treatment of occlusive vascular diseases, and in particular to improvements in anti-thrombotic therapy.

Thromboxane synthase inhibition has received much attention for its potential in the treatment of occlusive vascular diseases. However, a major problem following thromboxane synthase inhibition is an accumulation of prostaglandin endoperoxides which can occupy and activate the thromboxane receptors and thereby induce platelet aggregation and secretion. In contrast, thromboxane receptor antagonists, by blocking the thromboxane/endoperoxide receptor, prevent the action of both thromboxane $A_2$ and the endoperoxides on platelets and smooth muscle.

Our UK Patent Specification No. 2097397 describes inter alia [1R-[1α(Z),2β,3β,5α]]-(+)-7-[5-[[(1,1'-biphenyl)-4-yl]methoxy]-3-hydroxy-2-(1-piperidinyl)-cyclopentyl]-4-heptenoic acid (hereinafter referred to as Compound A). The compound is a potent thromboxane receptor blocker and thus antagonises the actions of thromboxane $A_2$, and, in particular, it inhibits thromboxane $A_2$ and endoperoxide mediated aggregation of blood platelets and contraction of vascular smooth muscle. It is thus of particular interest as an anti-thrombotic agent.

The present invention is based on our discovery that Compound A or a salt thereof (e.g. the hydrochloride salt) will act synergistically with a thromboxane synthase inhibitor to prevent blood platelet aggregation. In our experiments, using the test described by Lumley & Humphrey (J. Pharmacol. Methods, 1981, 6, 153–166) with collagen as the pro-aggregatory agent, we have shown that Compound A or a salt thereof (e.g. the hydrochloride salt) and a thromboxane synthase inhibitor such as 4-[2-(1H-imidazol-1-yl)ethoxy]benzoic acid (dazoxiben), (E)-7-phenyl-7-(3-pyridinyl)-6-heptenoic acid (CV 4151) or (E)-5-[[[(3-pyridinyl)[3-(trifluoromethyl)phenyl]methylen]amino]oxy]pentanoic acid (R 68070) can each inhibit platelet aggregation. However, when we have tested Compound A or a salt thereof (e.g. the hydrochloride salt) in the presence of thromboxane synthase inhibitors such as dazoxiben, CV 4151 or R 68070 in isolated human whole blood, we have found that the effectiveness of the combination in inhibiting collagen-induced aggregation is greater than with either agent alone and is greater than any simple additive effect one might expect when using two anti-aggregatory agents which interfere with the actions of thromboxane.

Thus, the use of Compound A or a salt thereof (e.g. the hydrochloride salt) with a thromboxane synthase inhibitor in combination therapy can be expected to be significantly more effective in the treatment of occlusive vascular diseases than is a thromboxane $A_2$ antagonist or a thromboxane synthase inhibitor alone.

Compound A or a salt thereof (e.g. the hydrochloride salt) and a thromboxane synthase inhibitor in combination therapy is therefore of interest for use in the treatment or prophylaxis of occlusive vascular diseases, including myocardial infarction, cardiac fatalities, angina, transient ischaemic attacks and cerebral infarction, atherosclerosis and vessel wall disease, peripheral vascular disease, nephropathy, diabetic retinopathy, postoperative thrombosis and pulmonary embolism, renal dialysis and peptic ulcer disease, peri- and postoperative complications following organ transplantation (particularly cardiac and renal), coronary artery bypass, peripheral artery bypass, angioplasty, thrombolysis and endarterectomy. Compound A or a salt thereof (e.g. the hydrochloride salt) and a thromboxane synthase inhibitor in combination therapy may also be of use in the treatment or prophylaxis of cyclosporin A-induced nephrotoxicity and in the treatment of asthma and adult respiratory distress syndrome.

According to one aspect of the invention we therefore provide the use of a composition containing as active ingredients Compound A or a physiologically acceptable salt or solvate thereof and a thromboxane synthase inhibitor in the therapy or prophylaxis of occlusive vascular diseases in human subjects.

In a further aspect of the invention, we provide a method of treating occlusive vascular diseases in human subjects which comprises administering to the patient effective amounts of Compound A or a physiologically acceptable salt or solvate thereof and a thromboxane synthase inhibitor in a single composition.

It will be appreciated that it is not necessary to administer Compound A or a salt or solvate thereof and the thromboxane synthase inhibitor as a single composition in order to achieve an improvement in efficacy. Providing that both compounds are present at the same time in the subject to be treated the compounds may be administered separately, Compound A or a salt or solvate thereof preferably being administered first, followed by the thromboxane synthase inhibitor.

In another aspect of the invention, therefore, we provide the use of Compound A or a physiologically acceptable salt or solvate thereof and a thromboxane synthase inhibitor in the presence of each other in the patient, for the therapy or prophylaxis of occlusive vascular diseases in human subjects.

In a further aspect of the invention we provide a method of treating occlusive vascular diseases in human subjects which comprises administering to the patient effective amounts of Compound A or a physiologically acceptable salt or solvate thereof and a thromboxane synthase inhibitor in two separate compositions.

According to another aspect of the present invention we provide a pharmaceutical composition containing as active ingredients Compound A or a physiologically acceptable salt or solvate (e.g. hydrate) thereof, and a thromboxane synthase inhibitor.

Suitable salts of Compound A for use in the compositions of the invention include acid addition salts derived from inorganic and organic acids, such as hydrochlorides, hydrobromides, sulphates, phosphates, maleates, tartrates, citrates, benzoates, 2-chlorobenzoates, p-toluenesulphonates, methanesulphonates, salicylates, fumarates, lactates, hydroxynaphthalenecarboxylates (e.g. 1-hydroxy- or 3-hydroxy-2-naphthalenecarboxylates) or furoates; or salts with suitable bases such as alkali metal (e.g. sodium and potassium), alkaline earth metal (e.g. calcium or magnesium), ammonium and substituted ammonium (e.g. dimethylammonium, triethylammonium, 2-hydroxyethyl dimethylammonium, piperazine, N,N-dimethylpiperazine, piperidine, ethylenediamine and choline) salts. A preferred salt of Compound A for use in the compositions according to the invention is the hydrochloride salt which is specifically described in UK Patent Specification No. 2127406.

Compound A and salts thereof may be prepared according to the methods described in UK Patent Specification No. 2097397.

The thromboxane synthase inhibitors for use in the compositions according to the invention may, in general, be any thromboxane synthase inhibitors which act in a synergistic manner with Compound A to effect inhibition of blood platelet aggregation. Suitable compounds may be determined empirically by testing a combination of each of the compounds with Compound A using the method of Lumley & Humphrey described herein.

Examples of known compounds which may be used with Compound A in compositions according to the invention include imidazoles, imidazopyridines and pyridines with thromboxane synthase inhibitory activity. Particular examples of imidazole compounds include those described in UK Patent Specification Nos. 2016452, 2025946, 2038821 and 2045244, European Patent Specification Nos. 3901 and 33432 and Japanese Patent Specification No. J61277670. Particular examples of imidazopyridine compounds include those described in UK Patent Specification No. 2101595. Particular examples of suitable pyridine compounds include those described in UK Patent Specification No. 2039903 and European Patent Specification Nos. 69521, 80154, 111997, 129051 and 221601.

Important thromboxane synthase inhibitors for use in the compositions of the invention include the following compounds of formula (1)

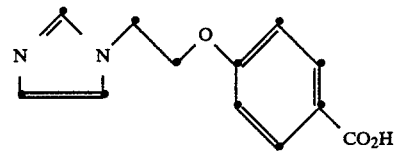

(a) (dazoxiben)

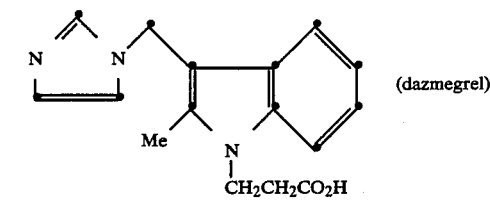

(b) (dazmegrel)

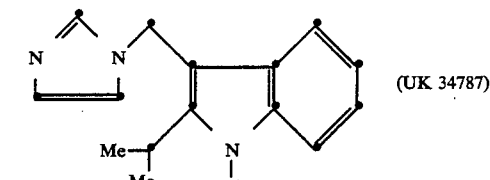

(c) (UK 34787)

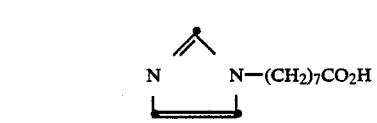

(d)

-continued

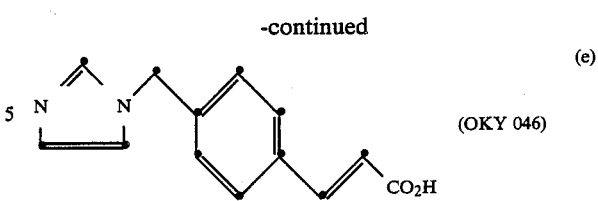

(e) (OKY 046)

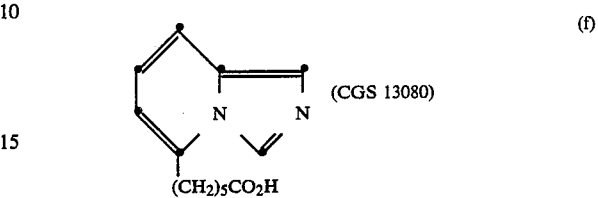

(f) (CGS 13080)

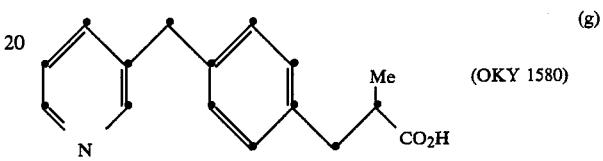

(g) (OKY 1580)

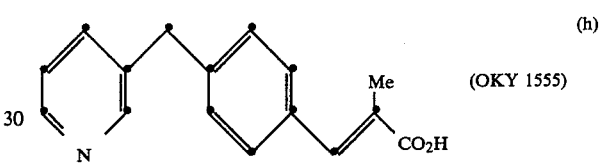

(h) (OKY 1555)

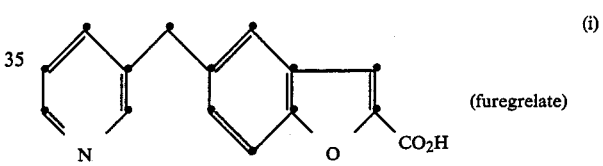

(i) (furegrelate)

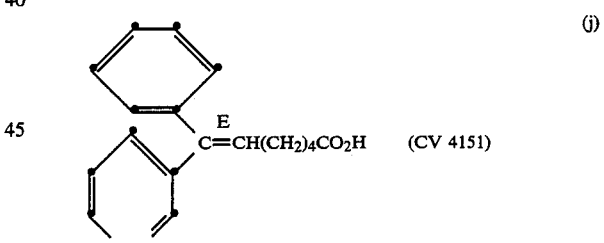

(j) (CV 4151)

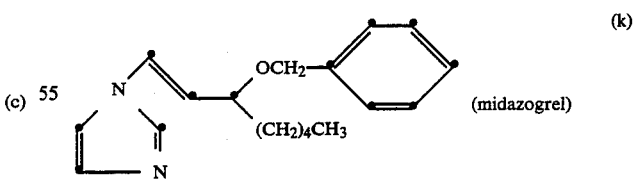

(k) (midazogrel)

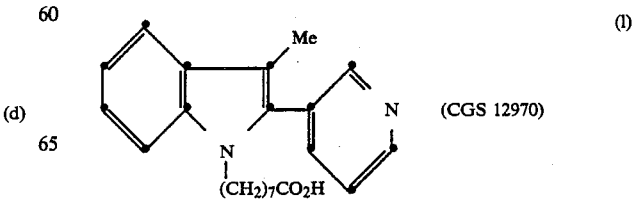

(l) (CGS 12970)

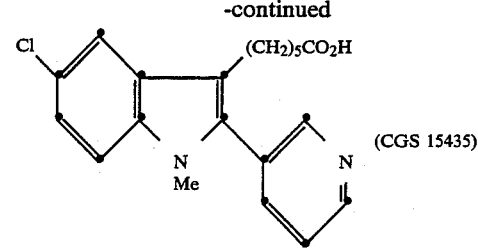

(m) (CGS 15435)

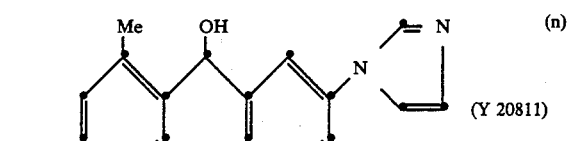

(n) (Y 20811)

and

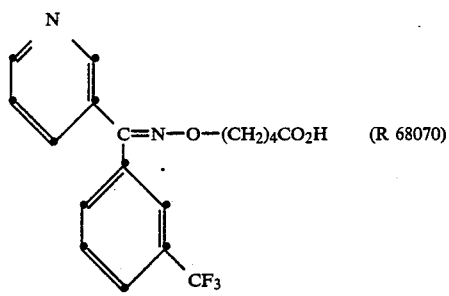

(o) (R 68070)

or a physiologically acceptable salt thereof.

Especially important compounds are the compounds of formulae 1(a), 1(b), 1(j) and 1(o), and, in particular, 1(j) and 1(o), and physiologically acceptable salts thereof.

Each of the compounds of formula (1) is described in one of the aforementioned UK, European and Japanese patent specifications and may be prepared by the methods described therein.

The relative proportions of Compound A and thromboxane synthase inhibitor employed in the compositions of the invention may generally be, for example, in the ratios by weight of about 25:1 to 1:10, in particular about 10:1 to 1:5 and especially about 1:1 of Compound A to synthase inhibitor.

The amount of Compound A employed in the compositions of the invention will preferably be in the range of 3.5 to 350 mg particularly 3.5 to 100 mg per dosage unit.

The amount of thromboxane synthase inhibitor employed in the compositions of the invention will preferably be in the range of 5 to 500 mg per dosage unit.

It is to be understood that when Compound A and the thromboxane synthase inhibitor are administered in two separate compositions the amount of Compound A employed in one composition and the amount thromboxane synthase inhibitor employed in the other composition will preferably be in the ranges given just above.

The precise dose administered of both Compound A and the thromboxane synthase inhibitor will of course depend on the age and condition of the patient. In general, the composition(s) will be administered in 1-4 doses per day.

According to a further aspect of the invention we provide a pharmaceutical composition containing as active ingredients Compound A or a physiologically acceptable salt or solvate (e.g. hydrate) thereof, and a thromboxane synthase inhibitor for use in the therapy or prophylaxis of occlusive vascular diseases in human subjects.

The compositions of the invention may be prepared by admixture of the active ingredients, and according to a further aspect of the present invention we provide a process for the preparation of a pharmaceutical composition comprising admixing Compound A or a physiologically acceptable salt or solvate thereof and a thromboxane synthase inhibitor.

The compositions of the invention may be presented with the aid of at least one pharmaceutical carrier or excipient. Thus, in a further aspect of the invention we provide a pharmaceutical composition comprising as active ingredients Compound A or a physiologically acceptable salt or solvate thereof and a thromboxane synthase inhibitor together with one or more pharmaceutical carriers or excipients.

In a still further aspect of the invention we provide a process for the preparation of a pharmaceutical composition which comprises admixing Compound A or a physiologically acceptable salt or solvate thereof and a thromboxane synthase inhibitor together with one or more pharmaceutical carriers or excipients.

The compositions may be in any forms suitable for administration, particularly for oral or parenteral administration.

The compositions may take the form of, for example, tablets, capsules, powders, solutions or syrups for oral administration. The compositions may thus contain as excipients, for example, binding agents, compression aids, fillers, lubricants, disintegrants and wetting agents. Tablets may be coated in a conventional manner, for example with a suitable film-forming material such as methyl cellulose or hydroxypropylmethyl cellulose. Alternatively the tablets may be sugar coated. Liquid preparations may also contain, for example, edible oils such as peanut oil.

For parenteral administration the compositions of the invention may take a form suitable for continuous infusion. Such forms include suspensions, solutions or emulsions in oil or aqueous vehicles, which may optionally contain formulatory agents such as suspending, stabilising and/or dispersing agents. Alternatively, the active ingredients may be in powder form for reconstitution before use with a suitable vehicle, e.g. sterile pyrogen-free water. Formulations for injections may be presented in unit dosage form in ampoules, or in multi-dose containers, with an added preservative, or in a suitable container for infusion.

The compositions of the invention may be prepared according to methods well known in the pharmaceutical industry. Thus, for example, tablets may be prepared by direct compression of the active ingredients blended with appropriate excipients. Alternatively, the blend of active ingredients and excipients may first be granulated using conventional techniques and the resulting granules compressed into tablets. Tablets may be film coated with suitable film forming materials using standard techniques.

Capsules may be prepared by blending the active ingredients and excipients and then filling the blend into gelatin capsules using a suitable filling machine.

Solutions for parenteral administration may be prepared by dissolving the active ingredients in a suitable vehicle e.g. water, and adjusting the tonicity and pH of the solution as required. The solution may if desired be clarified and then filled into appropriate sized ampoules. Sterilisation may be carried either before or after filling. If desired the solution may be packed under an inert atmosphere of nitrogen.

According to a still further aspect of the present invention we provide a composition containing as active ingredients Compound A or a physiologically acceptable salt or solvate thereof and a thromboxane synthase inhibitor for use in the manufacture of a medicament for the therapy or prophylaxis of occlusive vascular diseases in human subjects.

It may be convenient to present Compound A and the thromboxane synthase inhibitor as a two container pack, one container containing Compound A and the other containing the thromboxane synthase inhibitor. The compounds may then be admixed immediately before administration, or, if desired, may be administered sequentially.

The invention also provides Compound A or a physiologically acceptable salt or solvate thereof and a thromboxane synthase inhibitor and compositions containing them, in association with instructions for their use together in the therapy or prophylaxis of occlusive vascular diseases in human subjects.

When Compound A or a physiologically acceptable salt or solvate thereof and the thromboxane synthase inhibitor are administered in two separate compositions such compositions may be prepared according to methods described in the aforementioned UK, European and Japanese patent specifications. Alternatively, when Compound A or a physiologically acceptable salt or solvate thereof is to be administered as an aqueous formulation for, in particular, parenteral (e.g. intravenous) use the aqueous compositions may be prepared by mixing Compound A or, more preferably, the hydrochloride salt thereof with cyclodextrin together with one or more pharmaceutical carriers or excipients, for example as described in the Examples hereinafter. Preferably, Compound A or its hydrochloride salt are dissolved in water and the remaining constituents are added thereto.

The molar ratio of Compound A or its hydrochloride salt with the cyclodextrin in the aqueous composition is conveniently within the range 1:1 to 1:3.

The term "cyclodextrin" means herein an unsubstituted or substituted α-, β- or γ-cyclodextrin (or a hydrate thereof) or a mixture of two or three of them. Examples of suitable substituted cyclodextrins include sulphur-containing cyclodextrins, nitrogen-containing cyclodextrins, alkylated (e.g. methylated) cyclodextrins such as mono-, di- or trimethylated derivatives of a cyclodextrin (e.g. of β-cyclodextrin) and hydroxyalkyl (e.g. hydroxypropyl) cyclodextrins such as hydroxypropyl β-cyclodextrin and acylated derivatives thereof. Hydroxyalkyl (e.g. hydroxypropyl) cyclodextrins such as hydroxypropyl β-cyclodextrin have been found to be particularly suitable examples of substituted cyclodextrins.

Preferably, the aqueous formulation comprises the hydrochloride salt of Compound A and β-cyclodextrin (or a hydrate thereof) at about physiological pH wherein the formulation contains at least about 1.2 moles of β-cyclodextrin (e.g. 1.2 to 2 moles) for every one mole of the hydrochloride salt of Compound A. Preferably the molar ratio will be about 1:1.4.

The concentration of Compound A or the hydrochloride salt thereof in the aforementioned aqueous formulations suitable for parenteral administration, in particular for administration by injection (e.g. intravenously), is conveniently within the range 0.1–10 mg/ml, e.g. 0.1–5 mg/ml, expressed as the free base. Preferably, the concentration is 1 mg/ml expressed as the free base when the aqueous formulation is administered by intravenous injection. If desired, a higher concentration may be used and the solution may be diluted prior to use with, for example, an isotonic saline solution or dextrose or mannitol solution. Conveniently, solutions suitable for injection are presented in an appropriate dose volume (e.g. 1–100 ml). Dilutions suitable for continuous infusion may have a concentration of Compound A or its hydrochloride salt of 0.01–0.2 mg/ml expressed as the free base. The solution for continuous infusion may be presented in this form, for example in packs of 50–100 ml, or may be presented in more concentrated forms for subsequent dilution before use with, for example, an isotonic saline solution or dextrose or mannitol solution. Alternatively, small volumes of a more concentrated solution (e.g. 0.1–5 mg/ml) may be utilised for continuous infusion conveniently administered at a rate of 0.5 to 9.9 ml/h.

The aforementioned aqueous formulations may also be adapted for oral administration (e.g. as a capsule, syrup or solution). The preparation of suitable formulations for oral use will be within the knowledge of persons skilled in the art and may generally follow the procedures described in GB-B-2097397, GB-B-2127406 and in the Examples hereinafter.

The following Examples illustrate pharmaceutical compositions according to the invention and suitable aqueous formulations of the hydrochloride salt of Compound A. In the Examples the term 'Thromboxane A$_2$ Antagonist' means Compound A or a physiologically acceptable salt thereof, especially the hydrochloride salt. The term 'Thromboxane Synthase Inhibitor' means, for example, a compound of formula (1) or a physiologically acceptable salt thereof and is especially a compound of formula 1(a), 1(b), 1(j) or 1(o) and, in particular 1(j) or 1(o) or a physiologically acceptable salt thereof.

EXAMPLE 1

Pharmaceutical Examples of Parenteral Injections/Infusions Comprising the Hydrochloride Salt of Compound A (i) Hydrochloride Salt of Compound A, Equivalent to 50 mg Base

| β-Cyclodextrin hydrate | 143 mg | 166 mg | 238 mg |
|---|---|---|---|
| Sodium hydroxide solution | to pH 7 | to pH 7 | to pH 7 |
| Water suitable for injection | to 50 ml | to 50 ml | to 50 ml |

The hydrochloride salt of Compound A was dissolved in 35 ml water suitable for injection and the β-cyclodextrin was added. This solution was titrated to pH 7 with 0.02M sodium hydroxide solution and then adjusted to volume with water suitable for injection.

The solution may then be sterilised by filtration and filled into vials or ampoules.

(ii) Hydrochloride Salt of Compound A, Equivalent to 50 mg Base

| β-Cyclodextrin hydrate | 166 mg |
|---|---|

-continued

| | |
|---|---|
| Sodium chloride | 450 mg |
| pH 7.0 phosphate buffer | 2.5 ml |
| Sodium hydroxide solution | to pH 7 |
| Water suitable for injection | to 50 ml |

The hydrochloride salt of Compound A was dissolved in approximately 25 ml water suitable for injection. The $\beta$-cyclodextrin was dissolved therein and the resulting solution was titrated to pH 6 with 0.02M sodium hydroxide solution and the phosphate buffer added. The sodium chloride was added to the solution and the pH adjusted to pH 7 with sodium hydroxide. The solution was made up to volume with water suitable for injection. A sample of this solution was filled into a glass vial which was sealed with a rubber plug and metal overseal. This was then autoclaved.

(iii) Hydrochloride Salt of Compound A, Equivalent to 50 mg Base

| | |
|---|---|
| Hydroxypropyl-$\beta$cyclodextrin | 170 mg |
| Mannitol | 2.5 g |
| pH 6.0 phosphate buffer | 5.0 ml |
| Sodium hydroxide solution | to pH 6 |
| Water suitable for injection | to 50 ml |

The hydrochloride salt of Compound A was dissolved in approximately 25 ml water suitable for injection and the hydroxypropyl-$\beta$-cyclodextrin was added. The mannitol was then added and the solution titrated to pH 6 with 0.02M sodium hydroxide solution. The phosphate buffer solution was added and the solution adjusted to volume with water suitable for injection. The solution was then filtered and filled into glass vials which were sealed with rubber plugs and metal overseals. These were then autoclaved.

(iv) Hydrochloride Salt of Compound A, Equivalent to 50 mg Base

| | |
|---|---|
| $\beta$-Cyclodextrin hydrate | 166 mg |
| Mannitol | 2.5 g |
| Sodium acid phosphate | 46 mg |
| Disodium phosphate, anhydrous | 5 mg |
| Sodium hydroxide solution | to pH 6 |
| Water suitable for injection | to 50 ml |

The hydrochloride salt of Compound A was dissolved in approximately 25 ml water suitable for injection. The $\beta$-cyclodextrin and mannitol were dissolved therein and the solution titrated to pH 6 with 0.02M sodium hydroxide solution. The sodium acid phosphate and anhydrous disodium phosphate were dissolved in water suitable for injection. This solution was added to the bulk solution which was made up to volume with water suitable for injection. The solution was filtered and filled into glass ampoules which were sealed and then autoclaved.

| Hydrochloride salt of Compound A equivalent to 50 mg base | Cyclodextrin | | Mixture |
|---|---|---|---|
| | $\alpha$ | $\gamma$ | $\beta + \gamma$ |
| Cyclodextrin | 143 mg | 190 mg | 119 mg   136 mg |
| Mannitol | 2.5 g | g | 2.5 g |
| pH 6.0 Phosphate buffer | 5.0 ml | 5.0 ml | 5.0 ml |
| Sodium hydroxide solution | to pH 6 | to pH 6 | to pH 6 |
| Water suitable for injection | to 50 ml | to 50 ml | to 50 ml |

| Hydrochloride salt of Compound A equivalent to 50 mg base injection | Cyclodextrin | | Mixture |
|---|---|---|---|
| | $\alpha$ | $\gamma$ | $\beta + \gamma$ |

The hydrochloride salt of Compound A was dissolved in approximately 25 ml water suitable for injection and the cyclodextrin(s) was (were) added. The mannitol was then added and the solution titrated to pH 6 with 0.02M sodium hydroxide solution. The phosphate buffer solution was added and the solution was adjusted to volume with water suitable for injection. The solution was then filtered and filled into glass vials which were sealed with rubber plugs and metal overseals.

EXAMPLE 2

Pharmaceutical Example of an Oral Syrup Comprising the Hydrochloride Salt of Compound A Hydrochloride Salt of Compound A, Equivalent to 2.5 mg Base

| | |
|---|---|
| $\beta$-cyclodextrin hydrate | 9 mg |
| Citric acid | to pH 4.5 |
| Methyl hydroxybenzoate sodium | 5 mg |
| Propyl hydroxybenzoate sodium | 2 mg |
| Liquid orange flavour | qs |
| Sucrose | 3.25 g |
| Purified water | to 5.0 ml |

Dissolve the sucrose in a minimum quantity of water. Add the hydrochloride salt of Compound A and then the $\beta$-cyclodextrin with stirring; adjust the pH to 4.5 with citric acid. With continued stirring add a solution of the hydroxybenzoates and lastly the flavour. Adjust almost to volume with water and stir. Check the pH and adjust to 4.5 with citric acid if necessary. Make up to volume with water.

EXAMPLE 3

Preparation of a Tablet Containing Both Active Ingredients

| | mg/tablet |
|---|---|
| Thromboxane $A_2$ Antagonist | 20.0 |
| Thromboxane Synthase Inhibitor | 20.0 |
| Microcrystalline cellulose | 159.0 |
| Magnesium stearate BP | 1.0 |
| Compression weight | 200.0 mg |

The thromboxane $A_2$ antagonist and thromboxane synthase inhibitor are sieved and blended with the microcrystalline cellulose and magnesium stearate. The resulting mix is compressed on a suitable tablet machine using 8 mm punches. Tablets of other strengths may be prepared by altering the ratio of the active ingredients to microcrystalline cellulose or the compression weight and using punches to suit.

The tablets may be film coated with suitable film forming materials, such as hydroxypropyl methylcellulose, using standard techniques. Alternatively the tablets may be sugar coated.

Tablets may also be prepared by other conventional methods such as wet granulation.

EXAMPLE 4

Preparation of a Capsule Containing Both Active Ingredients

|  | mg/capsule |
| --- | --- |
| Thromboxane A<sub>2</sub> Antagonist | 20.0 |
| Thromboxane Synthase Inhibitor | 20.0 |
| Starch 1500* | 159.0 |
| Magnesium stearate BP | 1.0 |
| Fill Weight | 200.0 mg |

*a form of directly compressible starch

The thromboxane $A_2$ antagonist and thromboxane synthase inhibitor are sieved and blended with the Starch 1500 and the excipients. The mix is filled into size No. 2 hard gelatin capsules using suitable machinery. Capsules of other strengths may be prepared by altering the ratio of the active ingredients to Starch 1500 or the fill weight and if necessary changing the capsule size to suit.

We claim:

1. A method for the treatment or prophylaxis of occlusive vascular diseases in humans which comprises administering to the patient a synergistically effective amount of both (i) [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid or a physiologically acceptable salt or solvate thereof and (ii) a thromboxane synthase inhibitor, either separately or in combination.

2. The method according to claim 1 in which the compounds (i) and (ii) are administered as separate compositions for said use.

3. The method according to claim 1 in which compound (i) is in the form of its hydrochloride salt.

4. The method according to claim 1 in which compound (ii) is dazoxiben or dazmegrel or a physiologically acceptable salt thereof.

5. The method according to claim 1 in which compound (ii) is CV 4151 or a physiologically acceptable salt thereof.

6. The method according to claim 1 in which compound (ii) is R 68070 or a physiologically acceptable salt.

7. The method according to claim 1 in which the ratio of compound (i) to compound (ii) is about 1:1 by weight.

8. The method according to claim 1 in which compounds (i) and (ii) are in a form suitable for oral or parenteral administration.

9. The method according to claim 8, in which compounds (i) and (ii) are in the form of tablets, capsules or ampoules containing unit doses thereof.

10. A two-container pack for use in therapy or prophylaxis of occlusive vascular diseases in humans, one of the containers containing a synergistically effective amount of [1R-[1α(Z),2β,3β,5α]]-(+)-7-[5-[[(1,1'-biphenyl)-4-yl]methoxy]-3-hydroxy-2-(1-piperidinyl)-cyclopentyl]-4-heptenoic acid or a physiologically acceptable salt or solvate thereof and the other containing a synergistically effective amount of a thromboxane synthase inhibitor.

11. A pharmaceutical composition for use in therapy or prophylaxis of occlusive vascular diseases in humans, comprising a synergistically effective amount of [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid or a physiologically acceptable salt or solvate thereof and a thromboxane synthase inhibitor.

12. The composition of claim 11, wherein the thromboxane synthase inhibitor is an imidazole, imidazopyridine or pyridine thromboxane synthase inhibitor.

13. The composition of claim 12, wherein the heptenoic acid or physiologically acceptable salt or solvate thereof is present in a weight ratio to the thromboxane synthase inhibitor of from about 10:1 to 1:5.

14. The composition of claim 13, wherein the thromboxane synthase inhibitor is dazoxiben, dazmegrel or a physiologically acceptable salt thereof.

15. The composition of claim 13, wherein the thromboxane synthase inhibitor is a compound having the formula

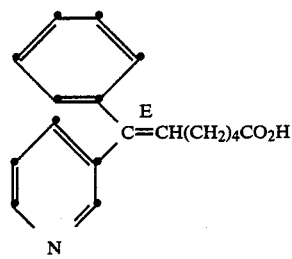

or a physiologically acceptable salt thereof.

16. The composition of claim 13, wherein the thromboxane synthase inhibitor is a compound having the formula

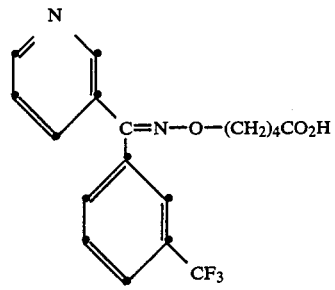

or a physiologically acceptable salt thereof.

17. The composition of claim 14, wherein the heptenoic compound is in the form of the hydrochloride salt.

18. The composition of claim 15, wherein the heptenoic compound is in the form of the hydrochloride salt.

19. The composition of claim 16, wherein the heptenoic compound is in the form of the hydrochloride salt.

* * * * *